United States Patent
Uno et al.

(10) Patent No.: US 11,848,091 B2
(45) Date of Patent: Dec. 19, 2023

(54) MOTION ESTIMATION SYSTEM, MOTION ESTIMATION METHOD, AND MOTION ESTIMATION PROGRAM

(71) Applicant: NEC Corporation, Tokyo (JP)

(72) Inventors: Yutaka Uno, Tokyo (JP); Masahiro Kubo, Tokyo (JP); Yuji Ohno, Tokyo (JP); Masahiro Hayashitani, Tokyo (JP); Yuan Luo, Tokyo (JP); Eiji Yumoto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 527 days.

(21) Appl. No.: 17/050,594

(22) PCT Filed: Apr. 26, 2018

(86) PCT No.: PCT/JP2018/017005
§ 371 (c)(1),
(2) Date: Oct. 26, 2020

(87) PCT Pub. No.: WO2019/207714
PCT Pub. Date: Oct. 31, 2019

(65) Prior Publication Data
US 2021/0241464 A1  Aug. 5, 2021

(51) Int. Cl.
*G16H 20/30* (2018.01)
*G06T 7/70* (2017.01)
(Continued)

(52) U.S. Cl.
CPC .......... *G16H 20/30* (2018.01); *G06F 18/214* (2023.01); *G06N 20/00* (2019.01); *G06T 7/20* (2013.01);
(Continued)

(58) Field of Classification Search
None
See application file for complete search history.

(56) References Cited

U.S. PATENT DOCUMENTS

2013/0271458 A1* 10/2013 Andriluka ............... G06V 40/23
                                                    345/619
2016/0314818 A1* 10/2016 Kirk .................... G06F 3/04845
(Continued)

FOREIGN PATENT DOCUMENTS

JP      2009-276886 A      11/2009
JP      2015-191471 A      11/2015
(Continued)

OTHER PUBLICATIONS

Japanese Office Action for JP Application No. 2020-515390 dated Jun. 14, 2022 with English Translation.
(Continued)

*Primary Examiner* — Leon Viet Q Nguyen (57) ABSTRACT

A motion estimation system 80 includes a pose acquisition unit 81 and an action estimation unit 82. The pose acquisition unit 81 acquires, in time series, pose information representing a posture of one person and a posture of another person identified simultaneously in a situation in which a motion of the one person affects a motion of the other person. The action estimation unit 82 divides the acquired time series pose information on each person by unsupervised learning to estimate an action series that is a series of motions including two or more pieces of pose information.

9 Claims, 4 Drawing Sheets (51) Int. Cl.
   *G06N 20/00* (2019.01)
   *G06T 7/20* (2017.01)
   *G06V 40/20* (2022.01)
   *G06F 18/214* (2023.01)
   *G06V 10/764* (2022.01)
   *G06V 20/40* (2022.01)
   *G06V 20/52* (2022.01)

(52) U.S. Cl.
   CPC .............. *G06T 7/70* (2017.01); *G06V 10/764* (2022.01); *G06V 20/49* (2022.01); *G06V 20/52* (2022.01); *G06V 40/20* (2022.01); *G06T 2207/10016* (2013.01); *G06T 2207/20081* (2013.01); *G06T 2207/30196* (2013.01)

(56) References Cited

U.S. PATENT DOCUMENTS

2017/0296129 A1* 10/2017 Petterson ............. A61B 5/7278
2018/0005129 A1* 1/2018 Moyerman ............. G06N 5/02

FOREIGN PATENT DOCUMENTS

| JP | 2015-207179 A | 11/2015 |
| JP | 2016-080671 A | 5/2016 |
| JP | 2016-118906 A | 6/2016 |
| JP | 2016-208516 A | 12/2016 |
| JP | 2017-156978 A | 9/2017 |
| JP | 2017-167878 A | 9/2017 |

OTHER PUBLICATIONS

International Search Report for PCT Application No. PCT/JP2018/017005, dated Jul. 24, 2018.

* cited by examiner

$$P = \begin{bmatrix} P_1^{th} & P_2^{th} & \cdots & P_t^{th} \\ P_1^{p} & P_2^{p} & \cdots & P_t^{p} \end{bmatrix} \quad A = \begin{bmatrix} A_1^{th} & A_2^{th} & \cdots & A_M^{th} \\ A_1^{p} & A_2^{p} & \cdots & A_m^{p} \end{bmatrix}$$

MOTION ESTIMATION SYSTEM, MOTION ESTIMATION METHOD, AND MOTION ESTIMATION PROGRAM

This application is a National Stage Entry of PCT/JP2018/017005 filed on Apr. 26, 2018, the contents of all of which are incorporated herein by reference, in their entirety.

TECHNICAL FIELD

The present invention relates to a motion estimation system, a motion estimation method, and a motion estimation program for estimating motions of a plurality of persons.

BACKGROUND ART

With the development of computer vision technology, it has become possible to measure motions without contact. Information representing the motions measured in this manner is utilized, for example, in educational settings, as learning data used by a robot or artificial intelligence (AI) to learn the motions.

Meanwhile, sequentially measuring and storing individual motions is a considerably time-consuming task. In order to eliminate such complexity of measuring and recording each motion, a method of segmenting the measured continuous motions is also known.

For example, Patent Literature (PTL) 1 describes a motion learning device that can segment continuous motions for learning. The learning device described in PTL 1 acquires a model from a plurality of pieces of time series data indicating continuous motions, generates a document containing discrete character strings represented by the model, and extracts and stores meaningful clauses from the character strings contained in the generated document.

PTL 2 describes a technique of recognizing work motions. In the system described in PTL 2, an analysis information division unit reads analysis information from an analysis information buffer by dividing the information in accordance with time stamps included in triggers, and an analysis unit performs analysis using the divided analysis information and a selected motion model. Specifically, the analysis unit calculates the degree of deviation indicating how far the motion indicated by the divided analysis information deviates from the selected motion model, and outputs the calculated degree of deviation as an analysis result.

CITATION LIST

Patent Literature

PTL 1: Japanese Patent Application Laid-Open No. 2009-276886
PTL 2: Japanese Patent Application Laid-Open No. 2017-156978

SUMMARY OF INVENTION

Technical Problem

Sequentially accumulating measured motions allows for quantification of the motions of an experienced person. Learning based on such quantified data can realize an AI that reproduces the motions of an experienced person.

The motions for which quantification is desired, however, are not limited to the motions of one user as described in PTL 1. For example, similar quantification is required for situations in which a person varies his/her response according to the other person's reaction.

One example of such situations is the motions of a therapist. As the number of stroke patients is increasing with aging, the importance of rehabilitation in patients with motor paralysis associated with stroke is also increasing. The reality, however, is that the number of therapists is not keeping pace with the increasing number of the patients.

Therapists' skills are often dependent on individuals and are difficult to systematize. Consequently, it takes a lot of time to pass on the skills to younger therapists. If therapists' motions can be quantified, it may be possible to realize an AI that assists transfer of the skills to younger therapists based on the rehabilitation records of veteran therapists.

The motion learning device described in PTL 1 may be used to quantify the treatment performed by a therapist on a patient as the therapist's motions. However, the therapist's motions vary dependent on the patient's response, so even if only the therapist's motions are quantified, it cannot be said that meaningful quantification has been performed.

That is, the motion learning device described in PTL 1 creates time series data according to the motions that a user has presented to a 3D motion capture camera. The device is thus based on the assumption that meaningful clauses are extracted on the basis of the motions of one person measured. It is thus difficult, even using the motion learning device described in PTL 1, to extract meaningful clauses from a plurality of persons' motions affecting each other.

The system described in PTL 2 merely accumulates motion time series data that has been simply divided on the basis of the triggers generated based on the trigger generation table. It is therefore necessary to set the trigger condition for each presumed motion in advance, and it is also difficult to divide the motions that do not meet the set conditions.

In view of the foregoing, it is an object of the present invention to provide a motion estimation system, a motion estimation method, and a motion estimation program that enable estimation of motions of individual persons from a situation in which the motions of the persons affect each other.

Solution to Problem

A motion estimation system according to the present invention includes: a pose acquisition unit configured to acquire, in time series, pose information representing a posture of one person and a posture of another person identified simultaneously in a situation in which a motion of the one person affects a motion of the other person; and an action estimation unit configured to divide the acquired time series pose information on each person by unsupervised learning to estimate an action series that is a series of motions including two or more pieces of pose information.

A motion estimation method according to the present invention includes: acquiring in time series, by a pose acquisition unit, pose information representing a posture of one person and a posture of another person identified simultaneously in a situation in which a motion of the one person affects a motion of the other person; and dividing, by an action estimation unit, the acquired time series pose information on each person by unsupervised learning to estimate an action series that is a series of motions including two or more pieces of pose information.

A motion estimation program according to the present invention causes a computer to perform: pose acquisition processing of acquiring, in time series, pose information representing a posture of one person and a posture of another person identified simultaneously in a situation in which a motion of the one person affects a motion of the other person; and action estimation processing of dividing the acquired time series pose information on each person by unsupervised learning to estimate an action series that is a series of motions including two or more pieces of pose information.

Advantageous Effects of Invention

The present invention enables estimation of motions of individual persons from a situation in which the motions of the persons affect each other.

DESCRIPTION OF EMBODIMENT

In the present invention, motions of a plurality of persons of interest are acquired and quantified. Specifically, in the present invention, only time series information on each person's posture (hereinafter, referred to as pose) is used to estimate a motion (hereinafter, referred to as action) as a subsequence of the pose time series and a series of actions (hereinafter, referred to as context), and symbols are assigned thereto. That is, an action represents a meaningful gathering of two or more poses, and an action series represents a gathering of time series of actions.

In this case, in the present invention, a situation is assumed in which the motion of one person affects the motion of another person (i.e., a situation in which the motions of a plurality of persons affect each other). With this, the motions affecting each other are documented from video that has captured a plurality of persons. As used herein, documentation is not limited to processing of explicitly defining the motions as a specific document; it also includes processing of converting the estimated actions and context into a database.

Further, in order to clarify the specific situation, the situation in which a therapist performs a treatment on a patient (rehabilitation treatment (hereinafter, referred to as rehabilitation) will be explained as an example below. This situation can be said to be a situation in which the therapist's motion affects the patient's motion (i.e., the motions of the therapist and patient affect each other). In this specific example, an action represents one act in rehabilitation, and an action series represents a series of acts of rehabilitation.

The situations in which the present invention is applied, however, are not limited to the situation involving the motions of the therapist and patient. Other situations may include, for example, situations in which the childcare worker's motion is expected to affect the child's motion and situations in which the athletes' motions affect each other. Further, the situations are not necessarily limited to the situations in which a plurality of persons perform motions in contact with each other. The present invention can also be applied to the situations in which non-contact motions affect each other.

An embodiment of the present invention will be described below with reference to the drawings.

Figure 1:
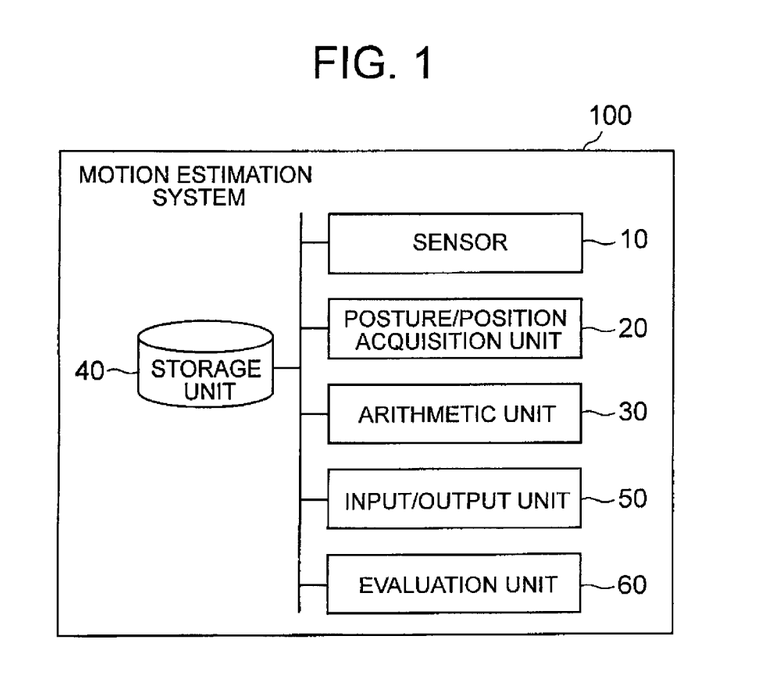
FIG. 1 is a block diagram depicting an exemplary configuration of an embodiment of a motion estimation system of the present invention.

FIG. 1 is a block diagram depicting an exemplary configuration of an embodiment of a motion estimation system of the present invention. A motion estimation system 100 of the present embodiment includes a sensor 10, a posture/position acquisition unit 20, an arithmetic unit 30, a storage unit 40, an input/output unit 50, and an evaluation unit 60.

The storage unit 40 stores various information and parameters required for the processing described later. The storage unit 40 also stores various information detected by the sensor 10 and estimated results of motions. The contents stored in the storage unit 40 will be described later. The storage unit 40 may be implemented by, for example, a magnetic disk or the like.

The sensor 10 acquires motions of a plurality of persons in time series. For example, in the case of acquiring the persons' motions as video, the sensor 10 may be implemented by an image sensor and a depth sensor. In this case, the sensor 10 may be configured to be included in an image pickup device (not shown) such as a 3D sensor camera. Further, for example in the case of acquiring the positions of parts of a person's body as coordinates, the sensor 10 may be implemented by a wearable sensor, for example. In this case, the sensor 10 may be configured to be included in a medium that can be attached to a person's body.

Since it is intended to acquire the motions of a plurality of persons, the sensor 10 is preferably capable of converting the motions into data by non-contact measurement. In the case of acquiring the motions of a plurality of persons as video, it is preferable that the video can be acquired from a plurality of directions by a plurality of image pickup devices because the presence of one person may conceal another person when the video is acquired from only one direction. In this case, the video acquired by the respective image pickup devices may be mapped to each other according to the positions where the image pickup devices are installed.

The posture/position acquisition unit 20 acquires information representing the poses of individual persons (hereinafter, referred to as pose information) in time series from the motions of a plurality of persons acquired by the sensor 10. That is, the posture/position acquisition unit 20 acquires, in time series, the poses of one person and another person identified at the same time.

Specifically, the posture/position acquisition unit 20 acquires individual persons' poses from the information acquired by the sensor 10. The way for the posture/position acquisition unit 20 to acquire the individual persons' poses is not limited. The posture/position acquisition unit 20 may recognize the poses of a plurality of persons using, for example, a learning-based classifier using the random forest.

For example, suppose that one person is a therapist and the other person is a patient. In this case, it can be said that the one and the other persons are apparently obvious from the images. In such cases, the posture/position acquisition unit 20 may acquire the poses of the respective persons by annotating only one image and then performing extrapolation on the subsequent images in a temporal direction.

The contents of the poses acquired by the posture/position acquisition unit 20 are not limited as long as they are uniform throughout the entire processing. For example, in the case where the sensor 10 is capturing video, the posture/position acquisition unit 20 may acquire the coordinates of the feature points (for example, joints of parts of the body) of each person in time series from the captured video. The acquired coordinates may be represented by, for example, vectors each indicating a pose at a time point. By connecting these coordinates, the skeleton of a person's shape can be identified. The pose information may also be referred to as a symbol string.

The information acquired by the posture/position acquisition unit 20 from video is not limited to the coordinates of the feature points. The posture/position acquisition unit 20 may acquire, for example, results of recognition of persons in the video, their states, situations, etc. The methods for acquiring a person's states, situations, etc. from video are widely known, so the detailed description will be omitted here.

Further, for example in the case where coordinates of the positions of the parts of a person's body are obtained by the sensor 10, the posture/position acquisition unit 20 may acquire the coordinates for each person in time series.

Figure 2:
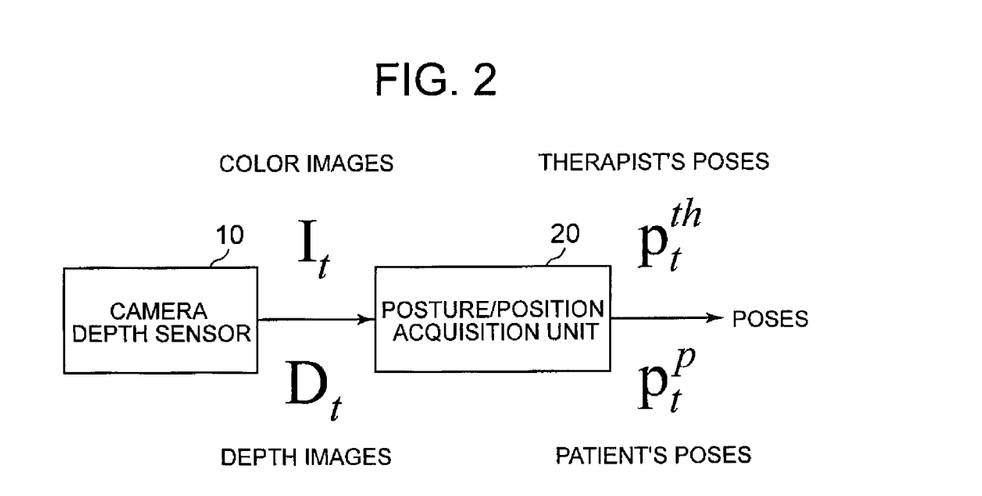
FIG. 2 is a diagram depicting an example of input/output data of a posture/position acquisition unit 20.

FIG. 2 is a diagram depicting an example of input/output data of the posture/position acquisition unit 20. When images are picked up with a camera including the sensor 10 implemented by a depth sensor, the posture/position acquisition unit 20 acquires color images $I_t$ and depth images $D_t$ in time series. Suppose that the images contain a therapist and a patient. At this time, the posture/position acquisition unit 20 outputs the therapist's poses $p_t^{th}$ and the patient's poses $p_t^P$ in time series.

The arithmetic unit 30 divides the acquired time series pose information on each person by unsupervised learning. The arithmetic unit 30 then estimates a series of motions including two or more pieces of pose information as an action series. In the following description, the information representing the estimated action series may also be referred to as a motion symbol string.

Figure 3:
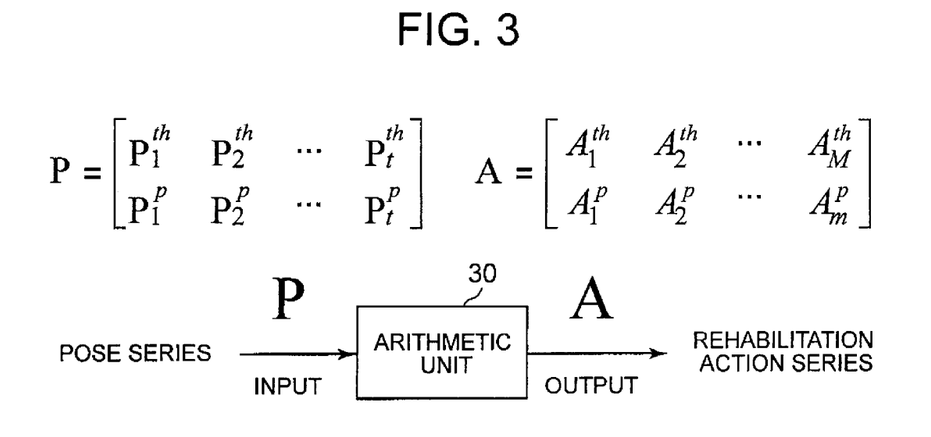
FIG. 3 is a diagram depicting an example of input/output data of an arithmetic unit 30.

FIG. 3 is a diagram depicting an example of input/output data of the arithmetic unit 30. When the poses acquired include the therapist's poses $p_t^{th}$ and the patient's poses $p_t^P$, a pose series P can be represented as a matrix containing two pose series. When the pose series P is input, the arithmetic unit 30 outputs an action series A with the respective poses divided. The example depicted in FIG. 3 indicates that the arithmetic unit 30 has generated M action series $A_M^{th}$ from the therapist's pose series $p_t^{th}$ and m action series $A_M^P$ from the patient's pose series $p_t^P$.

As described previously, each action includes one or more pieces of pose information. Thus, for example, the therapist's action series $A^{*th}$ can be represented as $A^{*th}=[p'^*_{-1}\ p'^*\ p'^*_{+1}]$.

It is assumed in the present invention that, for the pose information, actions, and a collection of actions acquired from a person's motions, the analogy of characters, words, and sentences (contexts) in a so-called natural language can be used to estimate each element in a similar manner. That is, it is assumed that the collection of actions is determined from the sequence of motion symbol string corresponding to the actions.

Suppose that in the present embodiment the motions themselves have been obtained with almost complete information from the time series of poses acquired by the posture/position acquisition unit 20. When adapted to the processing of natural language, it can be said that the arithmetic unit 30 performs the processing of writing and summarizing the time series of poses as a "sentence".

Further, in the present embodiment, the arithmetic unit 30 estimates the action series, not only from the pose information on one person, but also from the pose information on a plurality of persons. Estimating the action series of a plurality of persons in this manner enables quantification of the situation in which the motion of one person affects the motion of another person.

The problem to be solved here comes down to the problem of estimating characters (action primitives), words (actions), and sentences/context from a series of multi-dimensional poses (series of motions). As described previously, the present embodiment attempts to capture the motions by analogy with natural language, so the problem has a structure basically similar to that of the problem of estimating a gathering of morphemes, words, and sentences from a group of sentences written in a language, without a teacher.

Consider, for example, a situation in which a person is driving a car and about to turn left at an intersection. It can be understood that the context of "turning left" includes a series of actions such as "applying the brake to slow down", "turning on the direction indicator", "checking the left mirror", "viewing the left side", "turning the steering wheel to the left", "accelerating thereafter", and "returning the steering wheel". In such a situation, multi-dimensional time series of car posture and/or speed, driver manipulation, etc. can be segmented (divided) with appropriate granularity to estimate series of actions. Then, appropriate characters can be assigned to the actions, so that the original time series can be reduced to a lower dimension, converted into character strings, and summarized.

As a specific example, the arithmetic unit 30 divides the patient's pose series or the therapist's pose series independently into action series on the basis of hierarchical N-grams, using nonparametric Bayesian estimation. Alternatively, the arithmetic unit 30 divides the patient's pose series and the therapist's pose series simultaneously into action series on the basis of a multi-hierarchical N-gram model, using nonparametric Bayesian estimation. That is, the arithmetic unit 30 estimates the action series by solving a Bayesian model of performing hierarchical division of the pose time series into the action series according to nonparametric Bayes, similarly as the method of solving a Bayesian model of performing hierarchical division of words.

Here, suppose a pose time series $X=\{x_1, x_2, \ldots, x_n\}$. This pose time series X is a gathering of the pose time series of a plurality of persons generated individually. When an action series is represented as Z and an interaction between actions as S, a joint distribution p(X, Z, S) is represented as illustrated in the expression 1 below, using a conditional probability density function p(X|Z) of X determined by a parameter Z and a conditional probability density function p(Z|S) of Z determined by a parameter S.

$$p(X,Z,S)=p(X|Z)p(Z|S)p(S) \qquad \text{(Expression 1)}$$

In this case, a posterior probability p(Z, S|X) is represented according to the Bayesian theorem, and a marginal likelihood p(X) is represented by the joint distribution p(X, Z, S) with Z, S marginalized out, as illustrated in the following expressions 2 and 3, respectively.

$$p(Z,S|X)=p(X,Z,S)/p(X) \qquad \text{(Expression 2)}$$

$$p(X)=\int p(X,Z,S)dZdS \qquad \text{(Expression 3)}$$

The arithmetic unit 30 estimates an action series $Z=\{Z_{tj}\}$, S that maximizes the posterior probability p(Z, S|X) when a pose time series X is given. Specifically, the action series can be estimated by performing sampling from the posterior probability p(Z, S|X) using the Markov chain Monte Carlo method (or similar method). It should be noted that the statistical model used by the arithmetic unit 30 is not limited. The superiority or inferiority of estimated generative models can be compared, for example, by performing comparison between the models using an information criterion.

Further, the arithmetic unit 30 may estimate the action series from the divided motions, on the basis of the context representing the situation. For example, the same motion has different meanings according to the situations. For example, even in the case of the same motion of raising a lower limb in rehabilitation, it may be the motion intended for rehabilitation of the lower limb, or it may be the motion intended for rehabilitation of other parts with the lower limb kept at a fixed position, depending on the situations. The arithmetic unit 30 of the present embodiment may estimate the action series taking into consideration the context (i.e., the connection of preceding and following motions) representing such a situation.

Figure 4:
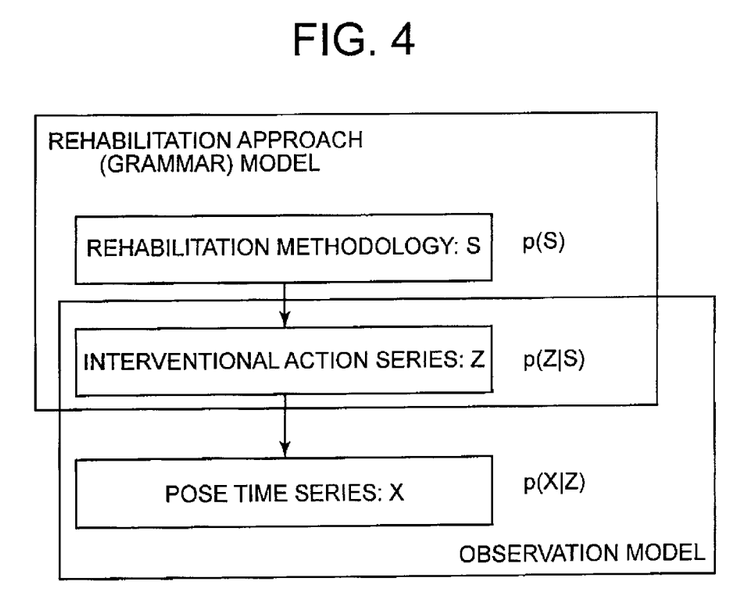
FIG. 4 is a diagram depicting an example of a model for generating a pose time series.

Specifically, in the case of rehabilitation described above, the pose time series generated by the statistical model can further be stratified by including an observational model that represents the actual observing and recording processes and a grammar model that is generated on the basis of the rehabilitation approach (context/situations). FIG. 4 is a diagram depicting an example of a model of generating a pose time series. As depicted in FIG. 4, an action series of rehabilitation, or, an intervention behavior series Z, is derived on the basis of a rehabilitation methodology S that represents interaction between the actions. The intervention behavior series Z is expressed as a set of pose time series X.

The arithmetic unit 30 stores the estimated action series in the storage unit 40. The way for the arithmetic unit 30 to retain the action series is not limited. As described previously, the arithmetic unit 30 may store the estimated action series as a symbol string in the storage unit 40. Further, the arithmetic unit 30 may store the date and time when the action was taken, the background information, and the like in association with the estimated action series in the storage unit 40.

For example, in the case of rehabilitation described above, the arithmetic unit 30 may store information identifying the therapist and patient involved in the captured rehabilitation and/or the outcome of the rehabilitation in association with the actions in the storage unit 40. Additional information that the arithmetic unit 30 may store in the storage unit 40 in association with the actions include documents representing text or images, including descriptions related to the rehabilitation, and medical record information, including information such as the patient's pathological conditions, laboratory values, and physician's diagnosis. In this manner, rehabilitation actions and outcomes are collected in a large scale and compiled into a database, so the information on rehabilitation stored in the storage unit 40 can also be called a rehabilitation corpus.

Accumulation of actions taken in rehabilitation and their consequences (outcomes) can also help identify more appropriate practices of rehabilitation. For example, by measuring the patient's motions before and after a single rehabilitation (e.g., walking task) and compiling the data, it is possible to estimate the effectiveness of the rehabilitation.

Further, by analyzing the rehabilitation corpus, the rehabilitation techniques based on the data can be systematized, which enables creation of an AI that imitates the techniques of excellent therapists. For example, for a particular intervention (rehabilitation intervention), the information stored in the storage unit 40 can be extracted to compare the distribution of outcomes for each intervention. This can help identify a rehabilitation intervention with more promising outcomes. Correspondence between such distributions and patients' pathological conditions may also be taken into consideration.

Various statistical models can be used for these analyses. For example, the motion estimation system 100 may include a learning unit (not shown) for deep-learning a function f that inputs background information such as the patient's pathological conditions, age, sex, brain image, and the like, and outputs an appropriate rehabilitation intervention (with, for example, maximum expected outcome gain).

That is, the rehabilitation corpus can be said to include information indicating the tacit knowledge and judgment abilities of excellent therapists. Therefore, learning the therapist AI using the rehabilitation corpus stored in the storage unit 40 allows for understanding of the suggestions of excellent therapists (for example, points of differentiation, points of intervention, and treatment plans).

The input/output unit 50 outputs information according to the estimated action series. The input/output unit 50 may accept labeling from a user for each action included in the estimated action series. Each action estimated in the present embodiment does not have an explicit label (i.e., the specific content of the action). By labeling each action as intended by the user, the contents of each action can be managed in a manner readily recognizable by the user.

Further, in the case where the posture/position acquisition unit 20 has acquired pose information in time series from video that has captured individual persons, the input/output unit 50 may output the estimated action series in association with the captured video. In this case, the input/output unit 50 may output in parallel the action series acquired from the same person at different times. Further, in this case, the input/output unit 50 may control the output of the video in units of estimated actions.

Figure 5:
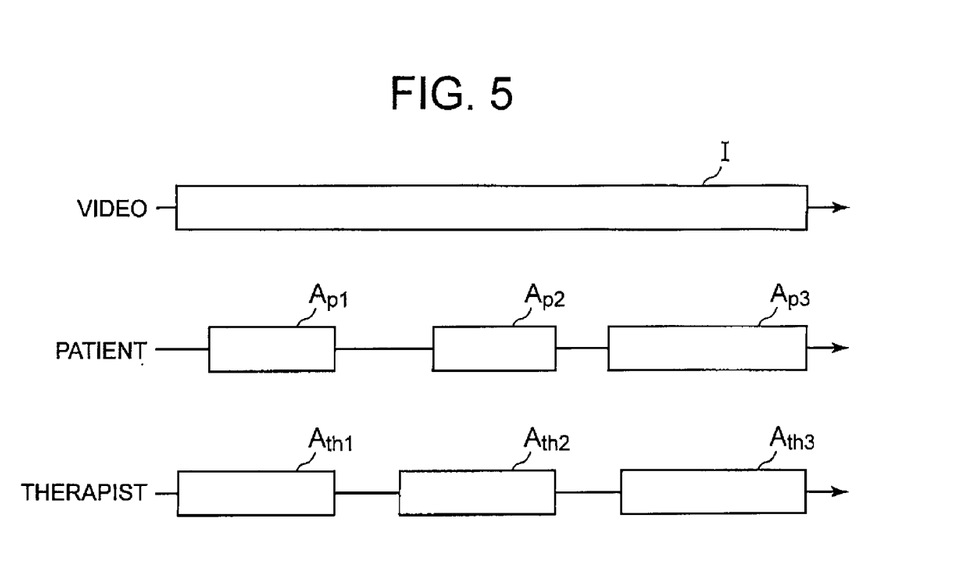
FIG. 5 is a diagram depicting an example of processing of outputting video in correspondence with estimated action series.

FIG. 5 is a diagram depicting an example of processing of outputting video in correspondence with estimated action series. For example, suppose that the sensor 10 has acquired video I depicted in FIG. 5. Here, suppose that the arithmetic unit 30 has estimated the patient's action series $A_{p1}$ to $A_{p3}$ and the therapist's action series $A_{th1}$ to $A_{th3}$. In this case, the input/output unit 50 may output the motions of both patient and therapist according to the time of the clipped pose information. Outputting the video in this manner makes it possible to navigate the actions with reference to the video.

The input/output unit 50 may also output estimated action series of same persons in parallel. Specifically, the input/output unit 50 may output action series of same persons, respectively, in parallel, among the same action series. Outputting the video in parallel in this manner allows changes of behaviors over time to be grasped at once. For example, in the case of rehabilitation, outputting the rehabilitation states of the same therapist and patient in parallel makes it possible to understand the patient's recovery at a glance.

The evaluation unit 60 evaluates motions of persons from the action series stored in the storage unit 40. Specifically, when the posture/position acquisition unit 20 newly acquires pose information on individual persons in time series, the evaluation unit 60 compares the acquired time series pose information with the actions included in the action series stored in the storage unit 40 to evaluate the motions of the individual persons.

The evaluation unit 60 may evaluate the motions of persons by adopting, for example, a method of giving higher rating for the higher degree of similarity between a matrix representing the time series pose information and a matrix representing the actions stored in the storage unit 40. In this case, the evaluation unit 60 may calculate, for example, that the smaller the difference between the corresponding elements when the respective matrices are normalized, the higher the degree of similarity therebetween. It should be noted that the method of evaluation and the method of calculating the degree of similarity illustrated herein are merely examples, and any method can be used as long as it can evaluate the proximity between the motions of persons and the action series stored in the storage unit 40. Such evaluation can increase the effectiveness of learning the motions to be modeled.

The posture/position acquisition unit 20, the arithmetic unit 30, the input/output unit 50, and the evaluation unit 60 are implemented by a CPU of a computer that operates in accordance with a program (the motion estimation program). For example, the program may be stored in the storage unit 40 of the motion estimation system, and the CPU may read the program and operate as the posture/position acquisition unit 20, the arithmetic unit 30, the input/output unit 50, and the evaluation unit 60 in accordance with the program. Further, the posture/position acquisition unit 20, the arithmetic unit 30, the input/output unit 50, and the evaluation unit 60 may each be implemented by dedicated hardware.

Figure 6:
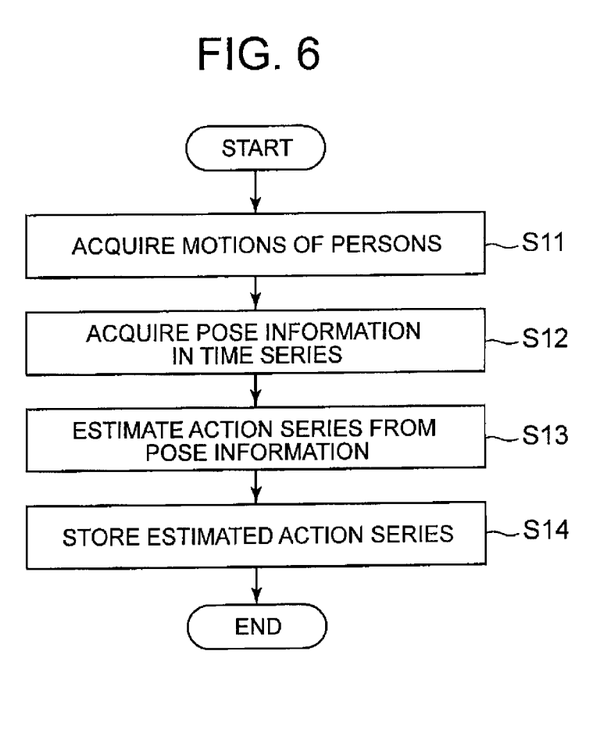
FIG. 6 is a flowchart depicting an exemplary operation of the motion estimation system.

An operation of the motion estimation system 100 of the present embodiment will now be described. FIG. 6 is a flowchart depicting an exemplary operation of the motion estimation system 100 according to the present embodiment. Firstly, the sensor 10 acquires motions of a plurality of persons simultaneously in a situation in which the motion of one person affects the motion of another person (step S11). The posture/position acquisition unit 20 acquires pose information on the one person and the other person in time series (step S12).

The arithmetic unit 30 divides the acquired time series pose information on the individual persons by unsupervised learning to estimate action series (step S13). The arithmetic unit 30 stores the estimated action series in the storage unit 40 (step S14).

As described above, in the present embodiment, the posture/position acquisition unit 20 acquires pose information representing the postures of one person and another person in time series, and the arithmetic unit 30 divides the acquired time series pose information on the individual persons by unsupervised learning to estimate the action series. This enables estimating the motions of a plurality of persons from a situation in which the motions of the respective persons affect each other.

For example, even if motions of individual persons are separately acquired and combined together, it will be difficult to increase the estimation accuracy of the motions that affect each other. On the other hand, in the present embodiment, the posture/position acquisition unit 20 simultaneously acquires the pose information on a plurality of persons, making it possible to accurately estimate the motions of the persons related to each other.

Further, for example in the method described in PTL 2, the motion time series are not discretized; rather, the degree of deviation or correlation of the motions is determined by calculating a certain kind of distance. On the other hand, in the present embodiment, the posture/position acquisition unit 20 and the arithmetic unit 30 discretize the motion series and assign the optimal symbols (symbols), and write the action series (of rehabilitation, for example) as a symbol string. For example, the symbol string of rehabilitation is obtained by imparting discrete symbols to the motion time series that quantifies the practice of rehabilitation. This also enables performing symbolic inference, unlike the case where the motion time series data is simply accumulated. Furthermore, as the arithmetic unit 30 records the rehabilitation symbol strings together with the information on the rehabilitation outcomes and electronic medical records in the storage unit 40, a database regarding rehabilitation (e.g., symptoms, rehabilitation performed, rehabilitation outcomes, etc.) can also be created.

Figure 7:
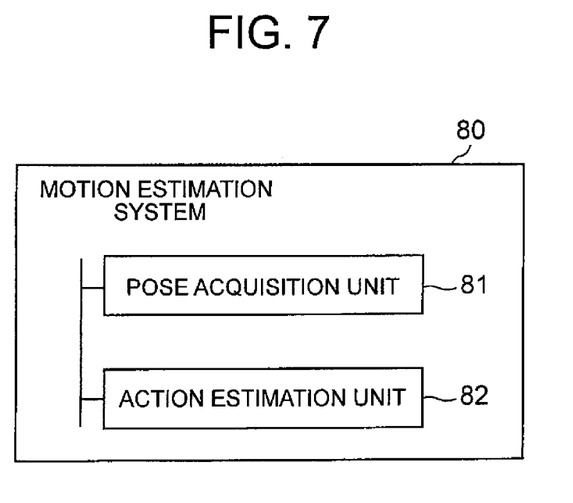
FIG. 7 is a block diagram depicting an outline of a motion estimation system according to the present invention.

An outline of the present invention will now be described. FIG. 7 is a block diagram depicting an outline of the motion estimation system according to the present invention. A motion estimation system 80 according to the present invention (for example, the motion estimation system 100) includes: a pose acquisition unit 81 (for example, the posture/position acquisition unit 20) that acquires, in time series, pose information representing a posture of one person (for example, a therapist) and a posture of another person (for example, a patient) identified simultaneously in a situation in which a motion of the one person affects a motion of the other person; and an action estimation unit 82 (for example, the arithmetic unit 30) that divides the acquired time series pose information on each person by unsupervised learning to estimate an action series that is a series of motions including two or more pieces of pose information.

Such a configuration enables estimation of the motions of a plurality of persons from a situation in which the motions of the persons affect each other.

The action estimation unit 82 may estimate the action series from the divided motions on the basis of a context (for example, a grammar model) representing the situation.

Specifically, the pose acquisition unit 81 may acquire, in time series, pose information on a therapist and a patient in rehabilitation. The action estimation unit 82 may then divide the acquired therapist and patient pose information to estimate the action series, and derive, from the estimated action series, an intervention behavior series as the action series of the rehabilitation on the basis of a rehabilitation methodology representing interaction between the actions.

The motion estimation system 80 may also include an output unit (for example, the input/output unit 50) that outputs information according to the estimated action series. The pose acquisition unit 81 may then acquire the pose information in time series from video that has captured the one person and the other person, and the output unit may output the estimated action series in association with the captured video. Such a configuration makes it possible to navigate the motions (actions) with reference to the video.

At this time, the output unit may control the output of the video in units of actions. Such a configuration allows the motions to be confirmed sequentially in units of actions.

The motion estimation system 80 may also include a storage unit (for example, the storage unit 40) that stores the estimated action series. The action estimation unit 82 may then store in the storage unit information identifying the one person and the other person in association with the estimated action series. Such a configuration enables the use of the storage unit storing the action series as a so-called rehabilitation corpus.

The motion estimation system 80 may also include an evaluation unit (for example, the evaluation unit 60) that evaluates the motions of persons from the action series stored in the storage unit. At this time, the pose acquisition unit 81 may newly acquire the pose information on each person in time series, and the evaluation unit may compare the acquired time series pose information with actions included in the action series stored in the storage unit to evaluate the motions of each person. Such a configuration can increase the effectiveness of learning the motions to be modeled.

The motion estimation system 80 may also include an input unit (for example, the input/output unit 50) that accepts labeling from a user for each action included in the estimated action series. Such a configuration allows the content of each action to be managed in a manner readily recognizable by the user.

INDUSTRIAL APPLICABILITY

The present invention is suitably applicable to a motion estimation system that estimates motions of a plurality of persons. For example, the present invention is suitably applicable to the case of converting rehabilitation interventions for improving efficiency of recovery rehabilitation into data.

REFERENCE SIGNS LIST

10 sensor
20 posture/position acquisition unit
30 arithmetic unit
40 storage unit
50 input/output unit
60 evaluation unit

The invention claimed is:

1. A motion estimation system comprising a hardware processor configured to execute a software code to:
   acquire, in time series, pose information representing a posture of one person and a posture of another person identified simultaneously in a situation in which a motion of the one person affects a motion of the other person, wherein the one person is a therapist and the other person is a patient in rehabilitation;
   divide the acquired time series pose information on each person by unsupervised learning;
   estimate an action series that is a series of motions including two or more pieces of the pose information, from the acquired time series pose information as has been divided, based on a context representing a situation of the one person and the other person; and
   derive an intervention behavior series of the rehabilitation based on the estimated action series.

2. The motion estimation system according to claim 1, wherein the intervention behavior series is derived based on a rehabilitation methodology representing interaction between actions of the estimated action series.

3. The motion estimation system according to claim 1, wherein
   the pose information is acquired in time series from video that has captured the one person and the other person, and
   the hardware processor is configured to execute the software code to further output the estimated action series in association with the captured video.

4. The motion estimation system according to claim 3, wherein the hardware processor is configured to execute the software code to further control the output of the video in units of actions.

5. The motion estimation system according to claim 1, further comprising a storage configured to store the estimated action series,
   wherein the hardware processor is configured to execute the software code to further store in the storage information identifying the one person and the other person in association with the estimated action series.

6. The motion estimation system according to claim 5, wherein the hardware processor is configured to execute the software code to further compare the acquired time series pose information with the actions included in the estimated action series stored in the storage to evaluate the motion of each person.

7. The motion estimation system according to claim 1, wherein the hardware processor is configured to execute the software code to further accept labeling from a user for each of a plurality of actions included in the estimated action series.

8. A motion estimation method comprising:
   acquiring in time series, by a processor, pose information representing a posture of one person and a posture of another person identified simultaneously in a situation in which a motion of the one person affects a motion of the other person, wherein the one person is a therapist and the other person is a patient in rehabilitation;
   dividing, by the processor, the acquired time series pose information on each person by unsupervised learning;
   estimating, by the processor, an action series that is a series of motions including two or more pieces of the pose information, from the acquired time series pose information as has been divided, based on a context representing a situation of the one person and the other person; and
   deriving, by the processor, an intervention behavior series of the rehabilitation based on the estimated action series.

9. A non-transitory computer readable information recording medium storing a motion estimation program that is executable by a processor to perform performs a method comprising:
   acquiring in time series, by a processor, pose information representing a posture of one person and a posture of another person identified simultaneously in a situation in which a motion of the one person affects a motion of the other person, wherein the one person is a therapist and the other person is a patient in rehabilitation;
   dividing, by the processor, the acquired time series pose information on each person by unsupervised learning;
   estimating, by the processor, an action series that is a series of motions including two or more pieces of the pose information, from the acquired time series pose information as has been divided, based on a context representing a situation of the one person and the other person; and
   deriving, by the processor, an intervention behavior series of the rehabilitation based on the estimated action series.

* * * * *